(12) United States Patent
Dang et al.

(10) Patent No.: US 9,867,932 B2
(45) Date of Patent: Jan. 16, 2018

(54) DRUG DELIVERY DEVICE HAVING A CAVITY SEALED BY A PRESSURIZED MEMBRANE

(71) Applicant: International Business Machines Corporation, Armonk, NY (US)

(72) Inventors: Bing Dang, Chappaqua, NY (US); John U Knickerbocker, Yorktown Heights, NY (US); Joana S. B. T. Maria, New York, NY (US); Bucknell C Webb, Yorktown Heights, NY (US); Steven L Wright, Cortlandt Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 152 days.

(21) Appl. No.: 14/928,546

(22) Filed: Oct. 30, 2015

(65) Prior Publication Data

US 2017/0119964 A1    May 4, 2017

(51) Int. Cl.
*A61M 5/168* (2006.01)
*A61M 5/142* (2006.01)
*A61M 5/44* (2006.01)
*A61M 5/172* (2006.01)

(52) U.S. Cl.
CPC .... *A61M 5/16804* (2013.01); *A61M 5/14276* (2013.01); *A61M 5/172* (2013.01); *A61M 5/44* (2013.01); *A61M 2205/0244* (2013.01); *A61M 2205/04* (2013.01); *A61M 2205/332* (2013.01); *A61M 2205/3561* (2013.01); *A61M 2205/50* (2013.01); *A61M 2207/00* (2013.01)

(58) Field of Classification Search
CPC .... A61M 5/16804; A61M 5/172; A61M 5/44; A61M 2205/332; A61M 2205/50; A61M 2207/00; A61K 9/0009; A61K 9/0024
USPC .......................................... 604/890.1; 216/2
See application file for complete search history.

(56) References Cited

U.S. PATENT DOCUMENTS

| | | | |
|---|---|---|---|
| 5,170,801 A | 12/1992 | Casper | |
| 5,527,288 A | 6/1996 | Gross | |
| 6,669,683 B2* | 12/2003 | Santini, Jr. .......... | A61K 9/0009 216/2 |
| 6,953,455 B2* | 10/2005 | Cho ..................... | A61K 9/0024 604/890.1 |
| 7,887,832 B2 | 2/2011 | First | |
| 8,221,354 B2 | 7/2012 | Haase | |
| 8,707,792 B2 | 4/2014 | Shekalim | |

(Continued)

OTHER PUBLICATIONS

Fernandes R et al., Self-folding polymeric containers for encapsulation and delivery of drugs. Adv Drug Deliv Rev. Nov. 2012;64(14):1579-89. doi: 10.1016/j.addr.2012.02.012. Epub Mar. 6, 2012. NIH reprint pp. 1-30 Nov. 2012.

(Continued)

*Primary Examiner* — Manuel Mendez
(74) *Attorney, Agent, or Firm* — Louis J. Percello; Otterstedt, Ellenbogen & Kammer, LLP

(57) ABSTRACT

A digital biomedical device includes a substrate forming a reservoir, a membrane comprising a first layer and a second layer having a strain therebetween, the membrane sealing the reservoir, and a controller configured to activate the membrane and release at least a portion of the strain causing the membrane curl and open the reservoir.

13 Claims, 7 Drawing Sheets

(56) References Cited

U.S. PATENT DOCUMENTS

| | | | |
|---|---|---|---|
| 2002/0183721 A1* | 12/2002 | Santini, Jr. | A61K 9/0009 604/890.1 |
| 2005/0267440 A1 | 12/2005 | Herman | |
| 2009/0306633 A1 | 12/2009 | Trovato | |
| 2010/0222802 A1 | 9/2010 | Gillespie, Jr. | |
| 2012/0017688 A1 | 1/2012 | Shekalim | |
| 2013/0338589 A1 | 12/2013 | Cindrich | |
| 2014/0323423 A1 | 10/2014 | DiPierro | |

OTHER PUBLICATIONS

Rob Matheson, "Major step for implantable drug-delivery device," MIT News, Jun. 29, 2015, pp. 1-6.

\* cited by examiner

_US 9,867,932 B2_

DRUG DELIVERY DEVICE HAVING A CAVITY SEALED BY A PRESSURIZED MEMBRANE

BACKGROUND

The present disclosure relates to medical devices, and more particularly to a pressurized membrane for a digital biomedical device.

Drug delivery devices are configured for timed release of units of medication from cavities etched into a substrate with ruptureable membranes. Utilizing handler technology and controlled atmosphere pressure, the drug delivery devices can be built with pressurized membranes. Once released, the pressure difference will help accelerate the diffusion into and out of the cavities. In this way, these drug delivery devices typically exhibit fast diffusion into and out of the cavities as compared to natural diffusion, which can affect the medication effect.

BRIEF SUMMARY

According to an exemplary embodiment of the present invention, a digital biomedical device includes a substrate forming a reservoir, a membrane comprising a first layer and a second layer having a strain therebetween, the membrane sealing the reservoir, and a controller configured to activate the membrane and release at least a portion of the strain causing the membrane curl and open the reservoir.

BRIEF DESCRIPTION OF THE SEVERAL VIEWS OF THE DRAWINGS

Preferred embodiments of the present invention will be described below in more detail, with reference to the accompanying drawings.

DETAILED DESCRIPTION

Biomedical devices are typically implanted into, worn on, or otherwise inserted in the body. The functions of a biomedical device can include medication delivery, sensor activation, etc.

According to an exemplary embodiment of the present invention, a digital biomedical device comprises a plurality of discrete, electronically-addressable structures (e.g., cavities or reservoirs). The structures can be disposed in an array. In one or more embodiments, a digital biomedical device includes a plurality of reservoirs containing a substance, e.g., a chemical or medication, which can be released into the body. In other embodiments, a digital biomedical device includes a plurality of cavities containing sensors for chemical activation or exposure to the body. Each structure is sealed with an electrically activated membrane or lid structure. The membrane or lid structure can be partially or completely opened under the control of the digital biomedical device.

According to an exemplary embodiment of the present invention, a digital biomedical device includes a pressurized sealing membrane disposed over a cavity, wherein the pressurized sealing membrane is configured to curl, thereby substantially opening to the cavity below. The pressurized sealing membrane is a stress engineered sealing membrane configured to curl away from a cavity once released. The pressurized sealing membrane is fixed with a differential stress and differential strain according to membrane material, thickness and dimensions. A pressurized sealing membrane can be released by edge fracturing, seal ring melting, fracturing and the like.

According to one or more embodiments of the present invention, the pressurized sealing membrane is configured to deflect once a seal is broken, which can indicate the hermeticity.

According to an exemplary embodiment of the present invention, the digital biomedical device achieves fast diffusion of fluid or medication into and out of cavities at least in part due to the substantial opening created by the released, curled, membrane. According to one or more embodiments of the present invention, pressure or stress is built into the pressurized sealing membrane upon sealing. Upon activation, the pressurized sealing membrane becomes a released membrane. The released membrane of the digital biomedical device can accelerate the diffusion of fluid or medication substance at least in part due to the substantial opening created by the released, curled, membrane (e.g., greater than 50% of the width of the cavity, greater than 75% of the width of the cavity).

Figure 1:
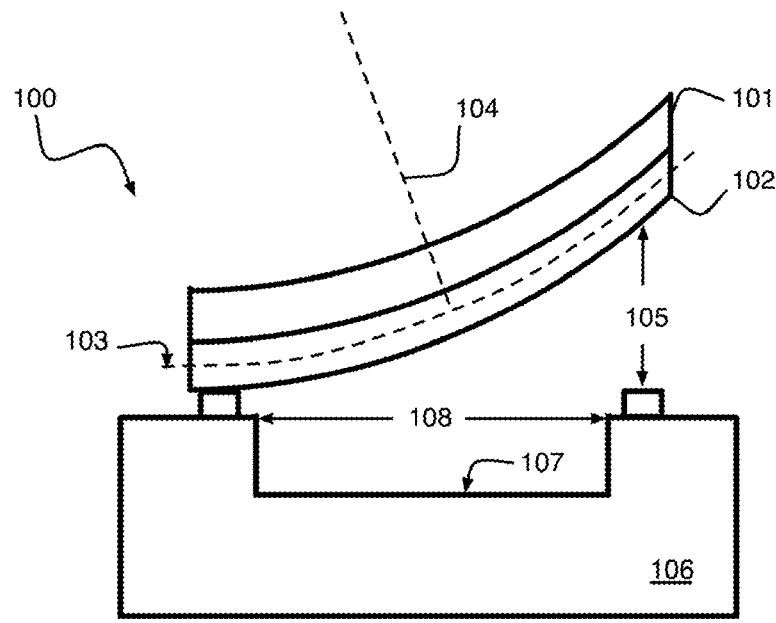
FIG. 1 is a diagram of a digital biomedical device according to an exemplary embodiment of the present invention.
Figure 2:
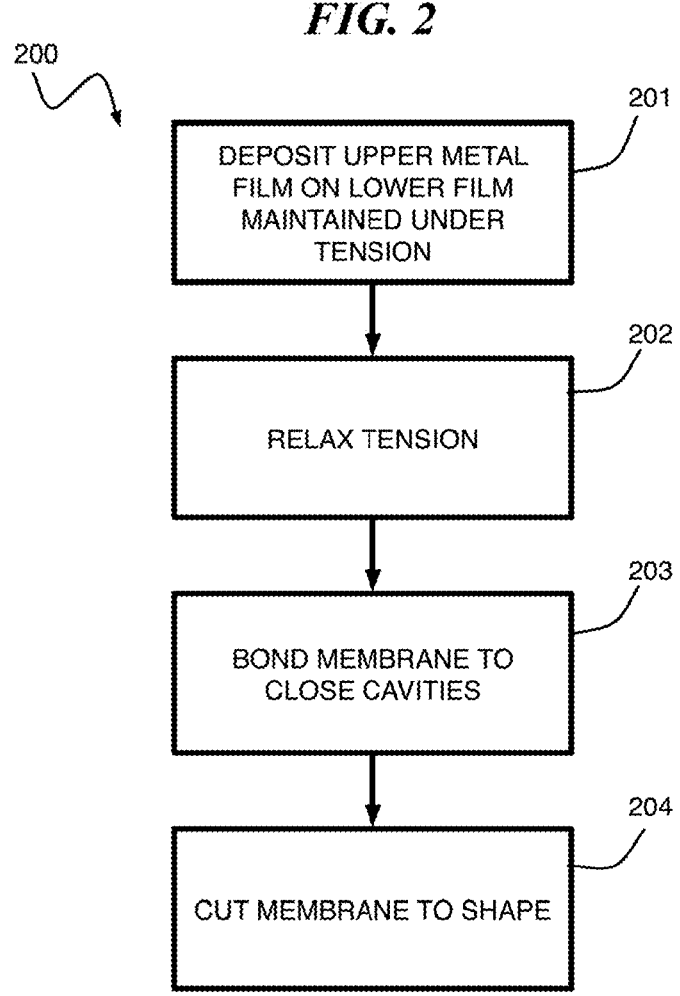
FIG. 2 is a flow diagram of a method for forming a membrane of a digital biomedical device according to an exemplary embodiment of the present invention.

According to an exemplary embodiment of the present invention, a membrane comprises a plurality of layer. For example, as shown in FIG. 1, a digital biomedical device 100 comprises a membrane including a first layer 101 having thickness t1 and a second layer 102 having thickness t2. The membrane is disposed over a cavity 107 of width L (108). The membrane open a distance d (105) with a bending radius R (103) of R=L*L/2d. In this example, for a cavity having a width of 300 um and a desired opening of at least 30 um, the radius of curvature must be less than 1.5 mm.

If t1=t2 and the moduli are the same, the bending radius is related to the relative difference in the length dL/L (initial strain) by R=t1/(d1/L). This sets a minimum initial strain in order to have a membrane of given thickness open a desired amount. This formula can be generalized using beam theory for arbitrary layering. In at least one exemplary embodiment, the parameters (e.g., thickness, initial strain, bending radius) of the membrane are determined using Stoney's theorem for thick coatings. Stoney's theorem is used to evaluate macro-stress acting in a coating deposited on a thick substrate.

According to an embodiment of the present invention, the initial strain can be created using one or more of a deposited film stress (choice of process and material), stretching the membrane during layer deposition, and thermal expansion differences. In the case of deposited film stress, the layers of the membrane will be thin, e.g., about 0.01 um to 10 um. In a closed state, a tensile stress is stored in an upper layer (e.g., first layer 101) of the membrane. A compressive stress is stored in a lower layer (e.g., second layer 102).

According to an embodiment of the present invention, strain is dimensionless. Strain can be measured as a percentage length change from a stress-less state. In a membrane having two layers of different lengths, the membrane is configured to roll-up in a manner that the shorter layer is inside and the longer layer outside. The membrane is initially held flat by the seal. When the seal is melted or broken the membrane rolls up. The tightness of the roll is limited by the length difference in the different layers, once it rolls up to a radius where the difference in length on the inside and outside of the roll is about equal to the length difference there is no stress to make the membrane roll tighter. If the membrane has an inherent stiffness it may stop rolling tighter before the stress is completely relieved.

Figure 3:
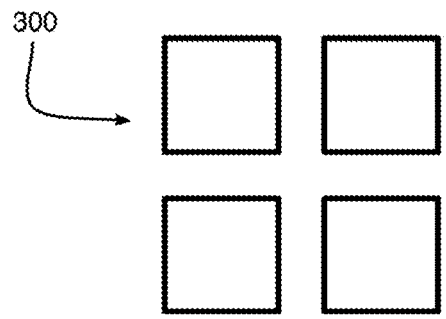
FIG. 3 is a diagram of a membrane formed as a lid of a digital biomedical device according to an exemplary embodiment of the present invention.
Figure 4:
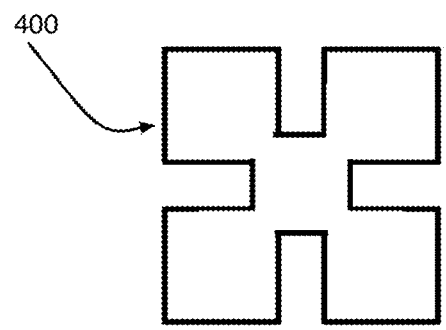
FIG. 4 is a diagram of a membrane formed as a plurality of lids of a digital biomedical device according to an exemplary embodiment of the present invention.
Figure 5:
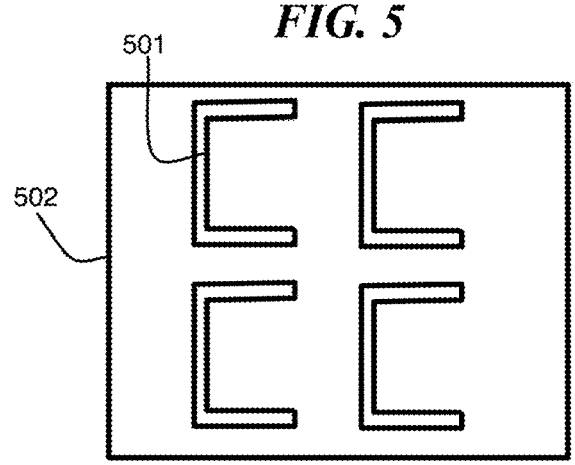
FIG. 5 is a diagram of a cut membrane configured to form doors of a digital biomedical device according to an exemplary embodiment of the present invention.

According to an embodiment of the present invention, a method for forming a membrane 200 includes placing a lower film under tension, while an upper metal film is deposited at 201. At block 202, tension is relaxed; the lower film is maintained in compression while the upper film is maintained in tension, but to a lesser degree than exists at block 201. At block 203, the membrane is bonded to a substrate having cavities formed therein, closing the cavities. At block 204, any excess membrane is cut into appropriate shapes (e.g., square, round, etc.) to form lids for the cavities, thereby forming a digital biomedical device. According to one or more embodiments of the present invention, the lids 300 can be formed to seal respective cavities (see FIG. 3), a plurality of lids can be linked into a group 400 (see FIG. 4), formed sealing a plurality of cavities, wherein doors (e.g., 501) are cut into the membrane 502 around respective cavities (see FIG. 5).

According to an embodiment of the present invention, the membrane is formed including a stretched organic membrane as the lower layer, with a deposited second layer as the upper layer. The lower layer can be formed as an organic material, such as kapton, mounted on a frame and mechanically stretched about 1% to 10% before the upper layer is deposited.

In at least one exemplary embodiment, a 1 millimeter layer of kapton is stretched 5% with 3000 A of Ti deposited thereon to achieve a membrane configured to curl with a radius around 0.5 millimeter.

In one or more embodiments, the lower layer is an organic material is mounted at an elevated temperature on a temporary handler having a different coefficient of thermal expansion (CTE). The upper layer is deposited on the organic material. At room temperature (i.e., a temperature lower than the elevated temperature used when the lower layer is mounted) the handler holds the organic material in a stretched condition, with the strain in the organic material determined by the difference in CTE between the organic material. For example, a material formed of a Polyethylene terephthalate (PET) lower layer and a Nickle (Ni) upper layer will curl with a radius of about 1.5 mm. This exemplary material can be formed by mounting the 60 ppm/C PET film on a 3 ppm/C temporary glass handler at 250° C. (below the melting point of the PET) (the glass handler having a length change of less than 0.1% over this temperature range), with the Ni deposited with a thickness of about 2000 Angstroms (A).

In the example of the PET lower layer, PET has about a 60 ppm/C CTE, and when bonded to the temporary glass handler that exhibits little thermal expansion below the melting point of PET which is 260 C, the PET exhibits a greater relative shrinking on cooling to 25 C (about 1.5%) so that the PET is held stretched until the PET is released from the temporary glass handler.

It should be understood that the temporary handler is a support to which a thin substrate is mounted, holding the thin substrate flat for processing. The temporary handler is attached with an adhesive that can be released later with solvent, heat or laser ablation (glass is used for its low CTE (3 ppm/C) and transparency to laser light).

In still another embodiment of the present invention, a curable or heat-setting lower layer organic material is deposited or spun onto on a temporary handler having a different CTE and is raised to an elevated temperature and hardened to fix the material structure. On cooling, the organic material is left in tension by the greater thermal expansion change in the organic material compared to the handler.

Figure 6:
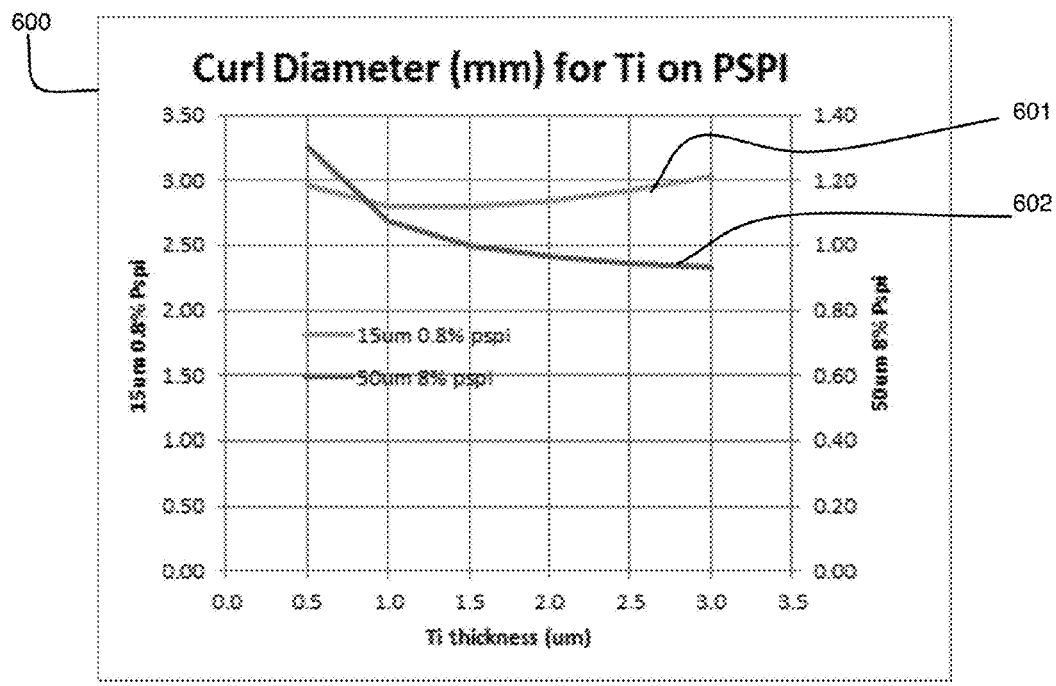
FIG. 6 is a graph of curl diameter of a membrane of a digital biomedical device according to an exemplary embodiment of the present invention.

FIG. 6 is a graph 600 showing a range of curl diameters for a membrane formed of Ti on a photosensitive polyimide (PSPI) according to an embodiment of the present invention. Curve 601 shows a curl diameter for different thicknesses of Ti on a 15 um layer of PSPI. Curve 602 shows a curl diameter for different thicknesses of Ti on a 50 um layer of PSPI.

According to an embodiment of the present invention, the membrane is formed by sequential deposition with introduced stress (e.g., by different CTE) of dissimilar oxide and metal materials to form a stack. For example, a 3 um silicon oxide is deposited as a base layer, and a second layer of SiN is deposited thereon having a thickness of 1000 A and a tensile strength of 700 megapascals (MPa). A length change of SiN having an offset strength of 300 Mpa is 700 MPa/Young's modulus (24 GPa) yielding a 0.25% length change. In this case, the radius of a curvature of a released membrane is about 4 mm.

Figure 7:
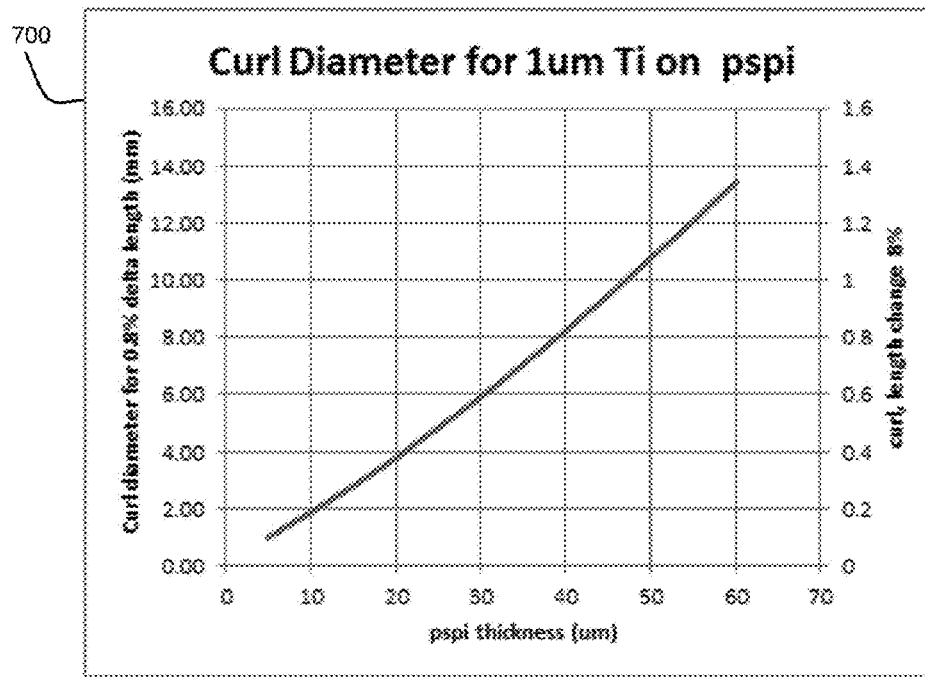
FIG. 7 is a graph of curl diameter of a membrane of a digital biomedical device according to an exemplary embodiment of the present invention.

FIG. 7 is a graph 700 showing a range of curl diameters for a membrane formed of 1 um of Ti on different thicknesses of PSPI according to an embodiment of the present invention.

As shown in FIG. 7, when a film curls or uncurls there is a length change (strain) proportional to the bilayer thickness and radius of curvature. The length change is zero at the bending plane, and the length change is linear from zero as dr/r, where the r is the radius of curvature and dr is the location in the film thickness away from the bending plane. In order for a stressed film to drive the bilayer to a given curvature, the film needs to be under stress even after the length change, this means that the pre-stretch or built in strain is larger than about thickness/r.

According to an embodiment of the present invention, the relationship between strain and stress for a material is stress=strain*modulus. According to an embodiment of the present invention, materials that can accommodate the needed strain without fracturing include plastics and organics. In at least one exemplary embodiment, the strain in the layers (one compressive, the other tensile) is greater than about 0.5%. Typical materials used in silicon (Si) processing such as oxides, nitrides, and non-annealing metals all yield or fracture below this strain.

According to an exemplary embodiment of the present invention, a large strain is desirable. One method of achieving the strain is to deposit an organic/polymer/plastic at elevated temperature on a low-thermal expansion substrate (silicon, low CTE glass, silicon nitride (SiN) . . . ) and rely on the thermal expansion shrinkage of the polymer to put the polymer into tension at room temperature. The CTE of polymers range from 20 ppm/C to 80 ppm/C. For example, SU-8 epoxy has a CTE of 50 ppm/C and can be deposited and hardened at 250° C. for a length change of about 1%. FIG. 6 and FIG. 7 show plausible metal thicknesses and radii.

Figure 8:
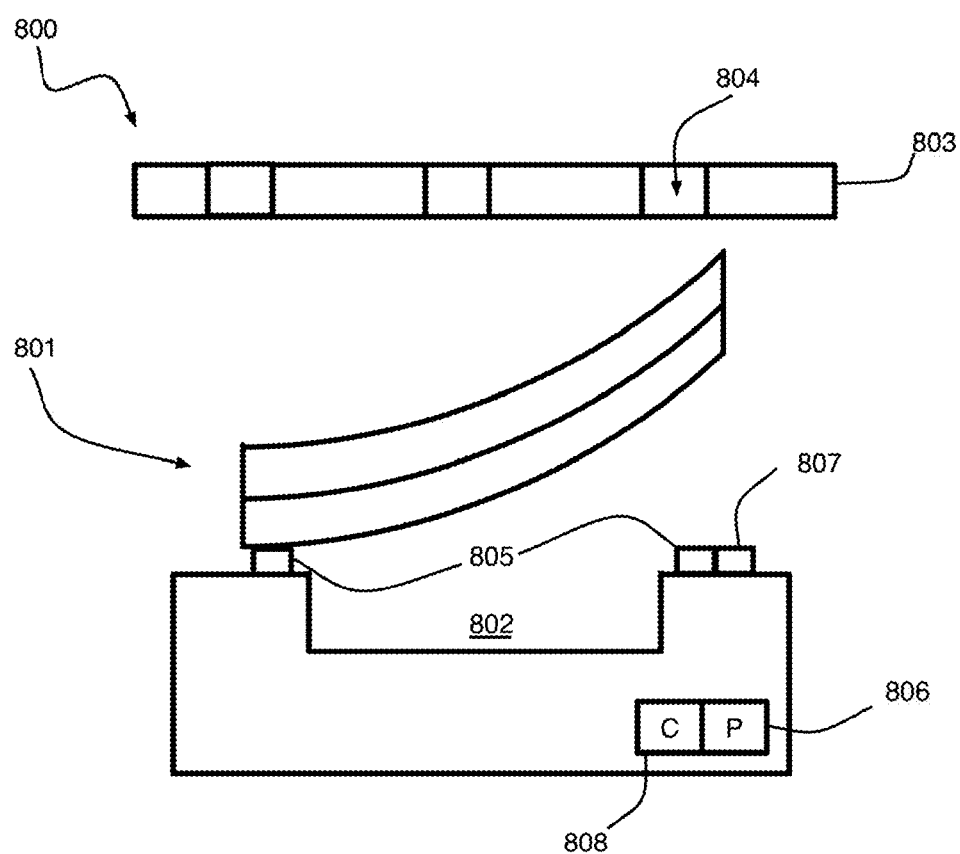
FIG. 8 is a diagram of a digital biomedical device according to an exemplary embodiment of the present invention.

According to an exemplary embodiment of the present invention, FIG. 8 shows a digital biomedical device 800 comprises a membrane 801 configured as a controllable component configured to release the contents of a cavity 802. The digital biomedical device 800 further comprises a cover 803 having pours 804. The cover 803 is configured as a porous protective cover.

The membrane 801 is held in a stressed position, with a strain between layers thereof. The membrane 801 seals the cavity 802, using seal 805 disposed around the cavity 802. The strain in the membrane 801 can be partially (at least) released by breaking at least a portion of a seal 805, allowing the membrane 801 to curl. In at least one embodiment of the present invention, the seal 805 is broken by applying heat, using a power source 806 and a heater element 807. The heater element 807 can be disposed adjacent to the seal 805 and/or in a portion of the seal 805. For example, the heater element can be a metal resistor configured to heat upon the application of an electric current from the power source 806. Furthermore, in at least one embodiment, the power source 806 is controlled by a controller 808, which can include a receiver for receiving a signal to activate the digital biomedical device 800. It should be understood that the controller 808 and the power source 806 can be disposed externally to the digital biomedical device 800, wherein an electrical lead is used to apply a current to the heater element 807.

According to an embodiment of the present invention, the seal 805 can be broken by other mechanisms, such as by dissolving in a liquid over time.

Figure 9:
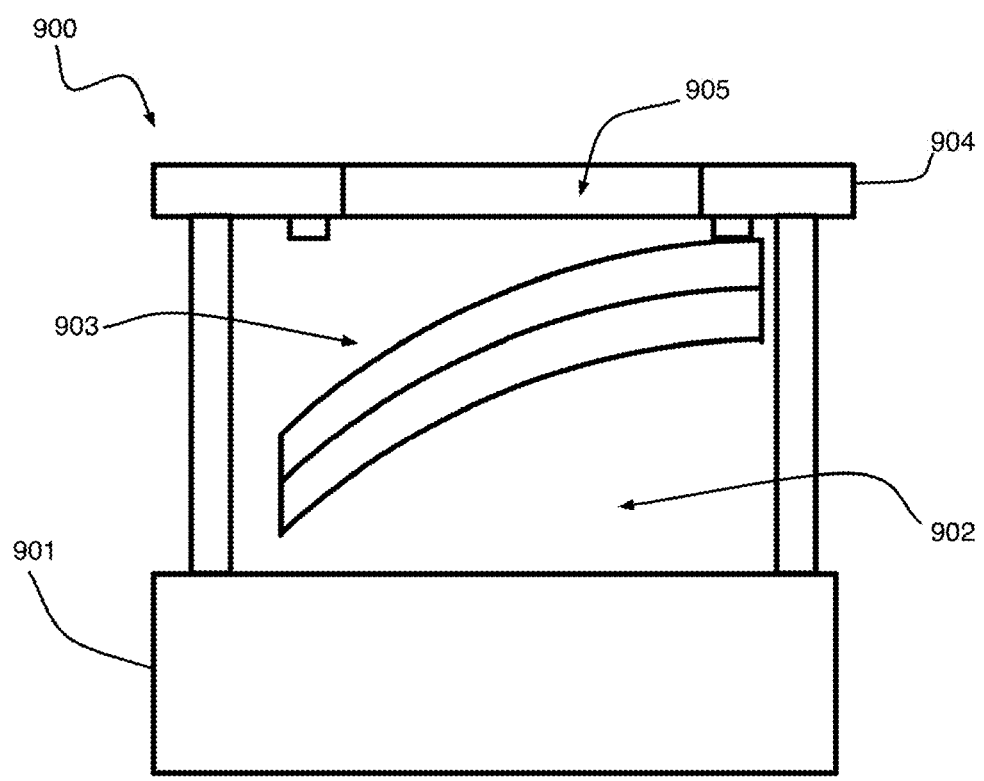
FIG. 9 is a diagram of a digital biomedical device according to an exemplary embodiment of the present invention.

According to an exemplary embodiment of the present invention, FIG. 9 shows a digital biomedical device 900 comprising a substrate 901, a cavity area 902, and a membrane 903 mounted on a cover 904. Upon activation, the membrane curls open exposing an opening 905 in the cover 904.

The methodologies of embodiments of the disclosure may be particularly well-suited for use in an electronic device or alternative system. Accordingly, embodiments of the present invention may take the form of an entirely hardware embodiment or an embodiment combining software and hardware aspects that may all generally be referred to herein as a "processor," "circuit," "module" or "system."

Furthermore, it should be noted that any of the methods described herein can include an additional step of providing a digital biomedical device including a membrane configured to curl, thereby opening a cavity below. Further, a computer program product can include a tangible computer-readable recordable storage medium with code adapted to be executed to carry out one or more method steps described herein, including the provision of the system with the distinct software modules.

Figure 10:
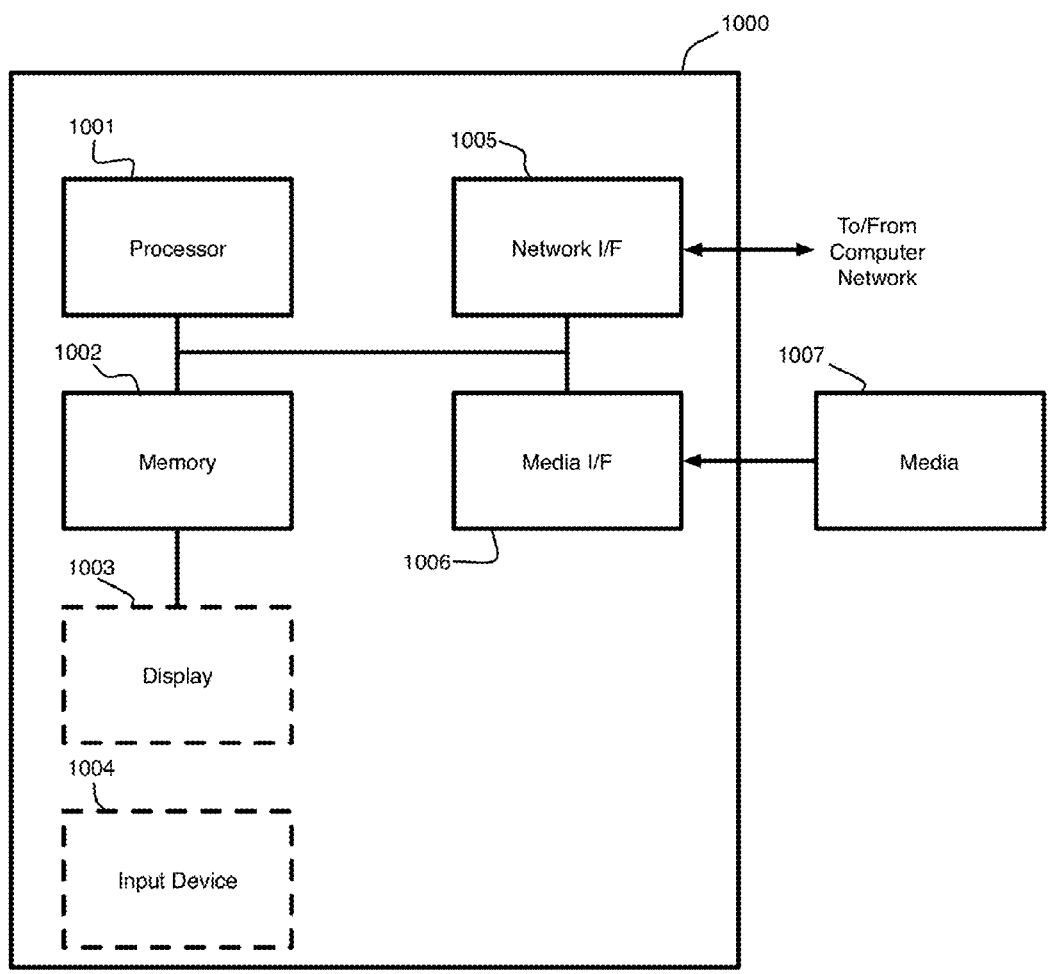
FIG. 10 is a block diagram depicting an exemplary computer system embodying the digital biomedical device.

Referring to FIG. 10; FIG. 10 is a block diagram depicting an exemplary computer system embodying the digital biomedical device (see for example, FIG. 8) according to an embodiment of the present invention. The computer system shown in FIG. 5 includes a processor 1001, memory 1002, display 1003, input device 1004 (e.g., keyboard), a network interface (I/F) 1005, a media I/F 1006, and media 1007, such as a signal source, e.g., camera, Hard Drive (HD), external memory device, etc.

In different applications, some of the components shown in FIG. 10 can be omitted. The whole system shown in FIG. 10 is controlled by computer readable instructions, which are generally stored in the media 1007. The software can be downloaded from a network (not shown in the figures), stored in the media 1007. Alternatively, software downloaded from a network can be loaded into the memory 1002 and executed by the processor 1001 so as to complete the function determined by the software.

The processor 1001 may be configured to perform one or more methodologies described in the present disclosure, illustrative embodiments of which are shown in the above figures and described herein. Embodiments of the present invention can be implemented as a routine that is stored in memory 1002 and executed by the processor 1001 to process the signal from the media 1007. As such, the computer system is a general-purpose computer system that becomes a specific purpose computer system when executing routines of the present disclosure.

Although the computer system described in FIG. 10 can support methods according to the present disclosure, this system is only one example of a computer system. Those skilled of the art should understand that other computer system designs can be used to implement embodiments of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A digital biomedical device comprising:
   a substrate forming a reservoir;
   a membrane comprising a first layer and a second layer having a strain therebetween, the membrane sealing the reservoir;
   a controller configured to activate the membrane and release at least a portion of the strain causing the membrane curl and open the reservoir;
   a sealing material disposed between the substrate and the membrane; and
   a heater element disposed in or adjacent to the sealing material, wherein the heater element is controlled by the controller to break the seal and allow the membrane to be curled by a bending moment caused by the strain difference between the first layer and the second layer of the membrane.

2. The digital biomedical device of claim 1, wherein the strain difference between the first layer and the second layer of the membrane is greater than about 0.5 percent.

3. A membrane sealing a reservoir of a digital biomedical device, the membrane comprising:
a first layer maintained having a compressive stress; and
a second layer bonded to the first layer and maintained having a tension,
wherein the first layer and the second layer have different lengths in a stress-less state, and wherein the first layer includes a polymer material and the second layer includes a metal material.

4. The membrane of claim 3, wherein a strain difference between the first layer and the second layer of the membrane is caused by different coefficients of thermal expansion of the first and second layers.

5. The membrane of claim 3, held in a substantially flat state to be a seal.

6. The membrane of claim 3, comprising a plurality of doors cut into the membrane around respective reservoirs.

7. A method of manufacturing a digital biomedical device comprising:
providing a substrate including a reservoir;
bonding a stress engineered sealing membrane to the substrate, the stress engineered sealing membrane comprising a first layer and a second layer having a strain therebetween, wherein the stress engineered sealing membrane sealing the reservoir; and
cutting the stress engineered sealing membrane around the reservoir.

8. The method of claim 7, wherein the strain difference between the first layer and the second layer of the membrane is greater than about 0.5 percent.

9. The method of claim 7, further comprising providing a controller configured to activate the stress engineered sealing membrane and release at least a portion of the stain, allowing the stress engineered sealing membrane to curl and open the reservoir.

10. The method of claim 9, further comprising:
providing an adhesive performing the bonding of the stress engineered sealing membrane to the substrate;
providing a heater element disposed adjacent to the adhesive; and
operating the controller to break a bond formed by the adhesive, allowing the stress engineered sealing membrane to curl by a bending moment caused by the strain difference between the first layer and the second layer of the membrane.

11. The method of claim 9, further comprising:
providing an adhesive performing the bonding of the stress engineered sealing membrane to the substrate;
providing a heater element disposed in the adhesive; and
operating the controller to break a bond formed by the adhesive, allowing the stress engineered sealing membrane to curl by a bending moment caused by the strain difference between the first layer and the second layer of the membrane.

12. The method of claim 7, wherein the cutting of the stress engineered sealing membrane around the reservoir forms a door having a plurality of sides around the reservoir.

13. The method of claim 7, wherein the cutting of the stress engineered sealing membrane around the reservoir forms a lid disposed over the reservoir.

* * * * *